United States Patent [19]

Yokoo et al.

[11] 4,256,631
[45] Mar. 17, 1981

[54] PROCESS FOR THE PREPARATION OF IMMUNOGLOBULIN FOR INTRAVENOUS ADMINISTRATION

[75] Inventors: Nobuo Yokoo, Sayama; Toshihito Mori, Higashimurayama, both of Japan

[73] Assignee: Kowa Company, Limited, Aichi, Japan

[21] Appl. No.: 131,539

[22] Filed: Mar. 18, 1980

[30] Foreign Application Priority Data

Mar. 22, 1979 [JP] Japan ................................ 54/33477

[51] Int. Cl.$^3$ ............................................... A23J 0/00
[52] U.S. Cl. .................................. 260/112 B; 424/85; 424/101; 424/177
[58] Field of Search .................... 260/112 B; 424/101, 424/177, 85

[56] References Cited

U.S. PATENT DOCUMENTS

| | | | |
|---|---|---|---|
| 2,770,616 | 11/1956 | Cohn | 260/112 B |
| 3,641,235 | 2/1972 | Weiss | 260/112 B UX |
| 4,046,722 | 9/1977 | Rowland | 260/112 B X |

FOREIGN PATENT DOCUMENTS 1247886 9/1971 United Kingdom .
1372953 11/1974 United Kingdom .

Primary Examiner—Howard E. Schain
Attorney, Agent, or Firm—Oblon, Fisher, Spivak, McClelland & Maier

[57] ABSTRACT

The specification describes an economical process for the preparation of immunoglobulin for intravenous administration. An immunoglobulin can be, in accordance with the process, purified by a combination of a fractional precipitation method and an affinity chromatography. As a precipitant, divalent or trivalent metal salts are used and a complex of human IgG and a polyhydroxy polymeric compound is employed as an adsorbent. Purified immunoglobulin contains little or no aggregated or partially denatured globulin which is believed to cause anaphylaxis when administered intravenously. Prior art techniques cannot economically provide immunoglobulin in such a purified form and only intramuscular injections were feasible. Intravenous administrations allow immunoglobulin to be dosed in a larger amount and to act much faster than intramuscular injections.

5 Claims, No Drawings

PROCESS FOR THE PREPARATION OF IMMUNOGLOBULIN FOR INTRAVENOUS ADMINISTRATION

This invention relates to a process for the preparation of immunoglobulin for an intravenous administration.

Human immunoglobulin has been used independently or in combination with antibiotics as a curative or a preventive mainly for agammaglobulinemia, viral infectious diseases (such as measles, rubella, polio, hepatitis and the like) and bacterial infectious diseases.

Immunoglobulin for clinical purposes has been heretofore produced from human plasma or placental blood as a starting material by the Cohn's alcohol fractionation or the like, but such a conventional immunoglobulin has been known to cause an anaphylactic shock when intravenously administered and has been thus forced to apply as an intramuscular injection.

The anaphylaxis is believed to result from the decomplimentation reaction caused by aggregated or partially denatured globulin which is produced during the steps of producing immunoglobulin or during the storage thereof.

However, the immunoglobulin application is accompanied by a pain on its intramuscular administration and cannot be administered in a large amount, coupled with another disadvantage that globulin molecules with a molecular weight of about 160,000 has a tendency of remaining at the site of administration over a long period of time after the administration, and its transmigration into blood is slow and little.

For the reasons mentioned above, there has been a demand for the development of immunoglobulin for an intravenous administration and studies have been made toward the preparation of an immunoglobulin, which shows a less tendency of the decomplementation reaction, by decomposing or removing aggregated or denatured globulin. As a result of such studies, the following methods have been proposed to treat the immunoglobulin obtained by, for example, the Cohn's fractionation: (1) to subject it to an enzymatical hydrolysis, using pepsin, plasmin, papain, bacterial proteases or the like; (2) to treat chemically it by an acid, propiolactone or the like; (3) to convert it into a chemical derivative by amidation, alkylation, S-sulfonation or the like; and (4) to subject it to a fractional precipitation, using polyethylene glycol or the like. Some of the resulting products are now clinically used.

However, among the above-mentioned methods, the method (1) is disadvantageous in that the activity of antibody is lowered and the half life time of the immunogloblin in blood is shortened, and the methods (2) and (3) have a disadvantage that the activity of antibody is lowered. To overcome such disadvantages, a method has been studied to remove denatured impurities alone while retaining the inherent properties of globulin, leading to the proposal of the method (4). In order to carry out this method, however, a large amount of polyethylene glycol or the like is required, throwing a problem of economy.

In view of the above, the present inventors have made an intensive study to prepare immunoglobulin free from the above-mentioned disadvantages and found that the decomplementarily-reacting substances can be efficiently eliminated by purifying immunoglobulin by a combination of a fractional precipitation method using one or more divalent or trivalent metal salts and an affinity chromatography using a complex of human IgG and a polyhydroxy polymeric compound. The present invention has been accomplished on the basis of the above finding.

According to the present invention, there is provided a process for the preparation of immunoglobulin for an intravenous administration. The process comprises purifying an immunoglobulin by a combination, in an arbitrary order, of a fractional precipitation method in which one or more divalent or trivalent metal salts are added to an aqueous solution of the immunoglobulin to collect the supernatant and an affinity chromatography using as an adsorbent a complex of human IgG and a polyhydroxy polymeric compound.

Among immunoglobulins to be usable as a starting material in the present invention, there are those obtained from human plasma or placenta by any one of known methods such as an alcohol fractionation, Rivanol fractionation, ammonium sulfate fractionation and the like, and immunoglobulin commercially available for intramuscular injection.

The process of the present invention is carried out, for instance, as follows.

The starting immunoglobulin is dissolved in water or an aqueous solution of a salt to a concentration of 1–20 w/v %, to which one or more divalent or trivalent metal salts are added in a concentration of $10^{-5}$ M–$10^{-2}$ M, followed by adjusting the pH to 5–9 to precipitate aggregated or denatured globulin causing the decomplementary reaction. Then, the precipitate is removed by a usual manner such as centrifugation, filtration or the like thereby collecting the supernatant.

The salts of divalent or trivalent metals used in the above process include, for example, chlorides, sulfates, phosphates, acetates, formates, carbonates, bicarbonates and the like salts of alkaline earth metals such as magnesium, calcium, barium, etc., and metals such as aluminium, tin, lead, iron, copper, zinc, etc.

Then, the thus-obtained supernatant is allowed to pass through a column filled with a complex of human IgG and a polyhydroxy polymeric compound, after which when the column is subjected to an elution with a salt solution or glycine solution of a low concentration, aggregated and/or denatured globulin causing the decomplementary reaction is adsorbed on the IgG of the carrier while immunoglobulin free of any decomplementarily-reacting substances is eluted.

As the polyhydroxy polymeric compound usable in the present process, there are, for example, agaroses such as Sepharose (trade mark, a product of Pharmacia Fine Chemicals), cellulose, dextrans such as Sephadex (trade mark, a product of Pharmacia Fine Chemicals), and glass beads such as CPG (trade mark, a product of Corning Glass Works). The complex of the polymeric compound and human IgG is easily prepared by a known method, e.g. by allowing the human IgG to act on the polymeric compound which has been activated with cyanogen bromide.

The salts usable for the eluate include the chlorides, sulfates, phosphates, acetates, formates, carbonates, bicarbonates and the like salts of alkali metals such as sodium, potassium, etc., alkaline earth metals such as calcium, magnesium, etc., and ammonium. The eluate is used generally in a concentration of 0.001–0.5 M, particularly 0.03–0.06 M.

The supernatant obtained by the fractional precipitation in accordance with the process of the present invention contains the metal ions employed and these ions have to be removed, for example, by a dialysis or ionexchange chromatography. This removal step may be conducted either prior to or after the affinity chromatography. In practice, it is convenient to dialyze the supernatant against the eluate employed for the affinity chromatography and then to subject the resulting solution to the affinity chromatography.

In order to obtain the intended immunoglobulin according to the present invention, it is essential to use the fractional precipitation procedure and the affinity chromatography in combination. The purpose of this invention is not satisfactorily achieved only by the application of either one of the procedures but the order of the combination may be determined optionally.

The column used for the affinity chromatography is washed with an eluate with an increased concentration of the salt to elute the decomplementarily-reacting substances adsorbed on the column, after which it can be re-used for a subsequent cycle of affinity chromatography.

As described hereinabove, the process of this invention is industrially advantageous as an extremely pure immunoglobulin can be produced in an economical manner by using inexpensive reagents and adsorbent.

The present invention will be described in more detail by way of the following reference and examples.

REFERENCE

Preparation of Adsorbent for Affinity Chromatography:

Ten milliliters of water was added to 10 ml of Sepharose 4B, to which was added 2 g of cyanogen bromide at 20° C. under stirring, followed by keeping its pH at 11 by the use of 5 N sodium hydroxide solution. After 5 minutes, the reaction solution was removed by filtration and the filtrate was sufficiently washed with a 0.1 M borate buffer of pH 8.0 and then suspended in the buffer. To the suspension was added an aqueous solution containing 200 mg of human IgG and, after allowing the mixture solution to stand at 5° C. overnight with stirring, 200 mg of glycerine was added to the mixture and stirred for further 1 hour. After the completion of the reaction, the solid content was collected on a glass filter and thoroughly washed with a physiological saline to obtain a complex of human IgG and Sepharose.

EXAMPLE 1

(a) Cohn Fractions II+III obtained from human placenta by the alcohol fractionation according to the Taylor et al.'s method [(see J. Am. Chem. Soc. 68, 459 (1972)] were rendered an about 5% aqueous solution. To 10 ml of the thus prepared solution (containing 540 mg of globulin) were added 10 μl of an aqueous 2% zinc sulfate solution and three droplets of an aqueous 0.5 N sodium hydroxide solution. The resulting precipitate was removed by centrifugation and the supernatant was dialyzed against a 0.04 M aqueous sodium chloride solution to obtain a solution containing 456 mg (at a recovery rate of 85%) of globulin (having a decomplementary value of 25 $C'H_{50}$). (b) The above solution (containing 456 mg of globulin) was diluted to 20 ml with a 0.04 M saline. The IgG-Sepharose affinity column (5 ml of Sepharose 4B containing 90 mg of IgG, 1.5×3 cm) obtained by the method of Reference was equilibrated with a 0.04 M saline, to which the above globulin solution was added for adsorption, followed by eluting the same with a 0.04 M saline and collecting the effluent by 2 ml. The fraction Nos. 3–11 were combined to obtain 350 mg of immunoglobulin (at a recovery rate of 77%) having a decomplementary value of 5 $C'H_{50}$.

EXAMPLE 2

The Cohn Fractions II+III of the same type as in Example 1 were dissolved in a physiological saline to give a concentration of about 5%. To 10 ml of the above solution (containing 520 mg of globulin) was added 0.2 ml of a 2% aqueous aluminum chloride solution, followed by adjusting its pH to 7.0 with an aqueous sodium phosphate solution. The resulting precipitate was removed by centrifugation and the supernatant was dialyzed against a 0.04 M sodium chloride solution to obtain a solution containing 416 mg (recovery rate of 80%) of globulin (with a decomplementary value of 30 $C'H_{50}$).

Thereafter, the procedure of Example 1(b) was followed and a solution of immunoglobulin free of the decomplementary reaction was resulted.

EXAMPLE 3

(a) In a 0.04 M saline was dissolved 500 mg of the Cohn Fractions II+III. The thus-prepared solution was subjected to an affinity chromatography in accordance with the same method as described in Example 1(b) and yielded a fraction containing 400 mg of globulin (at a recovery rate of 80%) having a decomplimentary value of 23 $C'H_{50}$.

(b) To 30 ml of the above fraction (which contains 400 mg of globulin) were added 20 μl of a 2% aqueous zinc sulfate solution and 20 μl of a 0.5 N aqueous sodium hydroxide solution. The resulting precipitate was removed by centrifugation. The supernatant contained 340 mg of globulin (recovery rate: 85%) having a decomplimentary value of 18 $C'H_{50}$.

It will be noted that the decomplementary values used in Examples were determined by measuring a degree of hemolysis according to the Kobat & Mayer's method [see Experimental Immunochemistry (2nd edition), C. C. Thomas Publisher (1961] by using sheep red blood cells and calculating the $C'H_{50}$ from the value of the degree of hemolysis.

What is claimed is:

1. A process for the preparation of immunoglobulin for an intravenous administration comprising purifying an immunoglobulin by a combination, in an arbitrary order, of a fractional precipitation method in which one or more divalent or trivalent metal salts are added to an aqueous solution of the immunoglobulin and the supernatant is collected, and an affinity chromatography using as an adsorbent a complex of human IgG and a polyhydroxy polymeric compound.

2. A process according to claim 1, wherein the fractional precipitation method comprises adding one or more divalent or trivalent metal salts to the aqueous immunoglobulin solution in a concentration of $10^{-5}$–$10^{-2}$ M, adjusting the pH of the solution to 5–9, and then collecting the supernatant.

3. A process according to claim 1, wherein the polyhydroxy polymeric compound is agarose, cellulose, dextran or glass beads.

4. A process according to claim 1, wherein the eluate for the affinity chromatography is a solution of an alkali metal, alkaline earth metal or ammonium salt or a glycine solution.

5. A process according to claim 4, wherein the concentration of the eluate is in the range of 0.001–0.5 M.

* * * * *